(12) United States Patent
Coppens et al.

(10) Patent No.: US 11,504,022 B2
(45) Date of Patent: Nov. 22, 2022

(54) MRI COMPATIBLE PATIENT TROLLEY

(71) Applicant: QFIX SYSTEMS, LLC, Avondale, PA (US)

(72) Inventors: Daniel Coppens, Avondale, PA (US); James Manning, Newark, DE (US); Franklin Ports, Jr., Conowingo, MD (US)

(73) Assignee: Qfix Systems, LLC, Avondale, PA (US)

( * ) Notice: Subject to any disclaimer, the term of this patent is extended or adjusted under 35 U.S.C. 154(b) by 64 days.

(21) Appl. No.: 17/317,224

(22) Filed: May 11, 2021

(65) Prior Publication Data
US 2021/0275051 A1 Sep. 9, 2021

Related U.S. Application Data

(63) Continuation of application No. 15/767,715, filed as application No. PCT/US2016/057108 on Oct. 14, 2016, now Pat. No. 11,039,758.
(Continued)

(51) Int. Cl.
*G01V 3/00* (2006.01)
*A61B 5/055* (2006.01)
(Continued)

(52) U.S. Cl.
CPC ............... *A61B 5/055* (2013.01); *A61G 1/02* (2013.01); *A61G 1/0287* (2013.01); *A61G 7/051* (2016.11);
(Continued)

(58) Field of Classification Search
CPC ........................................................ A61G 1/02
(Continued)

(56) References Cited

U.S. PATENT DOCUMENTS 3,304,116 A 2/1967 Stryker
3,344,445 A 10/1967 Crawford
(Continued)

FOREIGN PATENT DOCUMENTS

CN 1415272 A 5/2003
CN 2614662 Y 5/2004
(Continued)

OTHER PUBLICATIONS

Chinese Office Action for Chinese Application No. 201680071020.5, dated Apr. 3, 2020, with translation, 19 pages.
(Continued)

*Primary Examiner* — Walter L Lindsay, Jr.
*Assistant Examiner* — Frederick Wenderoth
(74) *Attorney, Agent, or Firm* — RatnerPrestia

(57) ABSTRACT

A trolley system configured to transport a patient within an MRI environment includes a patient support portion, a base portion configured for movement relative to a floor, a lift coupled to the patient support portion and the base portion, an electric motor coupled to the lift, and an electric blower coupled to the patient transfer device. The lift is configured to change the elevation of the patient support portion relative to the base portion. The motor is mounted such that the elevation of the motor is fixed relative to base portion. The trolley system is positionable adjacent an MRI apparatus within the MRI environment and the magnetic field of the MRI does not interfere with the operation of the motor or blower. The trolley system may further include a patient transfer device having an air bearing. The blower is configured to deliver air to the air bearing.

13 Claims, 6 Drawing Sheets

Related U.S. Application Data

(60) Provisional application No. 62/241,403, filed on Oct. 14, 2015, provisional application No. 62/241,400, filed on Oct. 14, 2015.

(51) Int. Cl.
*A61G 1/02* (2006.01)
*A61G 7/10* (2006.01)
*A61G 7/05* (2006.01)

(52) U.S. Cl.
CPC .......... *A61G 7/0508* (2016.11); *A61G 7/1001* (2013.01); *A61G 7/103* (2013.01); *A61G 7/1046* (2013.01); *A61G 7/0515* (2016.11); *A61G 7/0519* (2016.11); *A61G 2210/50* (2013.01)

(58) Field of Classification Search
USPC .......................................................... 324/318
See application file for complete search history.

(56) References Cited

U.S. PATENT DOCUMENTS

| | | |
|---|---|---|
| 4,175,783 A | 11/1979 | Pioth |
| 4,259,756 A | 4/1981 | Pace |
| 4,653,129 A | 3/1987 | Kuck et al. |
| 4,947,496 A | 8/1990 | Connolly |
| 4,949,410 A | 8/1990 | Failor et al. |
| 4,985,946 A | 1/1991 | Foster et al. |
| 5,179,744 A | 1/1993 | Foster et al. |
| 5,187,824 A | 2/1993 | Stryker |
| 5,522,100 A | 6/1996 | Schilling et al. |
| 5,604,942 A | 2/1997 | Allevato et al. |
| 5,733,247 A | 3/1998 | Fallon |
| 6,092,248 A | 7/2000 | Boemmel et al. |
| D456,751 S | 5/2002 | Williams |
| 6,936,030 B1 | 8/2005 | Pavlik et al. |
| 7,263,733 B2 | 9/2007 | Fujita et al. |
| 8,239,986 B2 | 8/2012 | Heimbrock et al. |
| 8,294,588 B2 | 10/2012 | Fisher et al. |
| 8,370,978 B2 | 2/2013 | Duvert |
| 8,656,528 B2 | 2/2014 | Perelman et al. |
| 9,021,634 B2 | 5/2015 | Goto et al. |
| 9,144,409 B1 | 9/2015 | Ocel et al. |
| 9,179,880 B2 | 11/2015 | Coppens et al. |
| 9,351,893 B2 | 5/2016 | Jei |
| 2001/0012914 A1 | 8/2001 | Kuth et al. |
| 2003/0070226 A1 | 4/2003 | Heimbrock |
| 2003/0159212 A1 | 8/2003 | Patrick et al. |
| 2004/0168254 A1 | 9/2004 | Rabska et al. |
| 2006/0059621 A1 | 3/2006 | Poulos et al. |
| 2006/0195984 A1 | 9/2006 | Hakamuin et al. |
| 2007/0089235 A1 | 4/2007 | Devinat et al. |
| 2008/0127416 A1 | 6/2008 | Tigwell |
| 2008/0173218 A1 | 7/2008 | Wang et al. |
| 2009/0024020 A1 | 1/2009 | Swaminathan et al. |
| 2009/0049613 A1 | 2/2009 | Dippl et al. |
| 2009/0232271 A1 | 9/2009 | Sendai |
| 2009/0249544 A1 | 10/2009 | Palay et al. |
| 2011/0009903 A1 | 1/2011 | Estrada |
| 2011/0163885 A1 | 7/2011 | Poulos et al. |
| 2011/0237960 A1 | 9/2011 | Rantala |
| 2012/0000016 A1 | 1/2012 | Dong et al. |
| 2012/0023666 A1 | 3/2012 | Heimbrock et al. |
| 2012/0102649 A1 | 5/2012 | O'Keefe |
| 2013/0150656 A1 | 6/2013 | Falk et al. |
| 2013/0239327 A1 | 9/2013 | Lemonnier et al. |
| 2013/0316624 A1 | 11/2013 | Diehl et al. |
| 2013/0340167 A1 | 12/2013 | Karwal et al. |
| 2014/0090168 A1 | 4/2014 | Coppens et al. |
| 2014/0187379 A1 | 7/2014 | Chen et al. |
| 2015/0135433 A1 | 5/2015 | Jei |
| 2016/0213538 A1 | 7/2016 | Sálus |
| 2016/0244184 A1 | 8/2016 | Alderman et al. |
| 2016/0270614 A1 | 9/2016 | Kawamura et al. |
| 2017/0055717 A1 | 3/2017 | Guthrie et al. |
| 2018/0168899 A1 | 6/2018 | Newkirk et al. |

FOREIGN PATENT DOCUMENTS

| | | | |
|---|---|---|---|
| CN | 2820084 Y | | 9/2006 |
| CN | 1969747 A | | 5/2007 |
| CN | 1990062 A | | 7/2007 |
| CN | 101032424 A | | 9/2007 |
| CN | 101150988 A | | 3/2008 |
| CN | 101375173 A | | 2/2009 |
| CN | 201192420 Y | | 2/2009 |
| CN | 101460099 A | | 6/2009 |
| CN | 101548194 A | | 9/2009 |
| CN | 101711700 A | | 5/2010 |
| CN | 101715309 A | | 5/2010 |
| CN | 201519238 U | | 7/2010 |
| CN | 102281855 A | | 12/2011 |
| CN | 102309321 A | | 1/2012 |
| CN | 202161495 U | | 3/2012 |
| CN | 102551978 A | | 7/2012 |
| CN | 202409301 U | | 9/2012 |
| CN | 202875639 U | | 4/2013 |
| CN | 103462689 A | | 12/2013 |
| CN | 203468903 U | | 3/2014 |
| CN | 203564433 U | | 4/2014 |
| CN | 103892910 A | | 7/2014 |
| CN | 104068982 A | | 10/2014 |
| CN | 204033627 U | | 12/2014 |
| CN | 204050076 U | | 12/2014 |
| CN | 104582666 A | | 4/2015 |
| CN | 204379573 U | | 6/2015 |
| DE | 202007004182 U1 | | 5/2007 |
| GB | 975226 | | 11/1964 |
| JP | 2006223605 A | * | 8/2006 |
| WO | 2013153493 A1 | | 10/2013 |
| WO | 2014055655 A1 | | 4/2014 |
| WO | 2015023731 A2 | | 2/2015 |
| WO | WO-2017066616 A1 | * | 4/2017 .......... A61B 5/0046 |

OTHER PUBLICATIONS

Chinese Office Action for Chinese Application No. 201680071020.5, dated Jul. 1, 2019, 19 pages.

Chinese Office Action for Chinese Application No. 201680071020.5, dated Oct. 23, 2020, with translation, 21 pages.

Chinese Office Action for Chinese Application No. 201680072417.6, dated Apr. 1, 2021 with translation, 21 pages.

Chinese Office Action for Chinese Application No. 201680072417.6, dated Apr. 3, 2020, with translation, 45 pages.

Chinese Office Action for Chinese Application No. 201680072417.6, dated Jul. 2, 2019, 33 pages.

Chinese Office Action for Chinese Application No. 201911155907.4, dated Dec. 2, 2020 with translation, 19 pages.

Decision of Rejection for Chinese Application No. 201680072417.6, dated Nov. 3, 2020, with translation, 36 pages.

European Communication for European Application No. 16 788 342.0, dated Nov. 21, 2019, 6 pages.

European Communication for European Application No. 16 788 343.8, dated Mar. 7, 2019, 7 pages.

European Communication for European Application No. 19 156 260.2, dated Apr. 20, 2020, 6 pages.

Extended European Search Report for European Application No. 19 156 260.2, dated Mar. 20, 2019, 8 pages.

Final Office Action for U.S. Appl. No. 15/767,517, dated Dec. 24, 2020, 49 pages.

International Preliminary Report on Patentability for International Application No. PCT/US2016/057108, dated Apr. 17, 2018—8 pages.

International Search Report and Written Opinion for International Application No. PCT/US2016/057108, dated Jan. 24, 2017—9 pages.

International Search Report and Written Opinion for International Application No. PCT/US2016/057123, dated Jun. 7, 2017, 22 pages.

(56) References Cited

OTHER PUBLICATIONS

Non Final Office Action for U.S. Appl. No. 15/767,517, dated Apr. 7, 2020, 27 pages.
Entire patent prosecution history of U.S. Appl. No. 15/767,715, filed Apr. 12, 2018, entitled, "MRI Compatible Patient Trolley."

* cited by examiner

MRI COMPATIBLE PATIENT TROLLEY

CROSS-REFERENCE TO RELATED APPLICATIONS

This application is a continuation of pending application Ser. No. 15/767,715, filed Apr. 12, 2018, which is a U.S. National Phase Application of PCT International Application PCT/US2016/057108, filed on Oct. 14, 2016, which claims the benefit of U.S. provisional patent application entitled "MRI COMPATIBLE PATIENT TROLLEY," which was filed on Oct. 14, 2015 and assigned Ser. No. 62/241,403, and U.S. provisional patent application entitled "PATIENT TROLLEY AND PATIENT TRANSFER DEVICE," which was filed on Oct. 14, 2015 and assigned Ser. No. 62/241,400. The entire contents of the foregoing provisional applications are incorporated herein by reference in their entirety.

FIELD OF THE INVENTION

The present invention generally relates to patient trolleys, associated systems, and methods for transporting patients and providing safe transfer of a patient from the patient trolley to a target modality during medical procedures or diagnostic determinations.

BACKGROUND OF THE INVENTION

Patient trolleys are used frequently in hospitals and treatment centers to safely transport patients to various locations within the facility. When the patient requires therapy or diagnostic imaging, the patient trolleys are used to deliver the patient in proximity to certain target modalities. Target modalities may include various patient support surfaces associated with machines, such as CT, MR, and PET, an operating table, a hospital bed, an OR table, a treatment machine, robotic surgical arms, etc. Patient trolleys are expected to safely transport a patient to and from various target modalities. Often these patients must be immobilized to maintain positional accuracy and consistency from one modality to the next.

In order to transfer a patient from the top surface of a patient trolley to the surface of a target modality, patient transfer devices are commonly used. For patients that are not ambulatory and are expected to remain lying down, including in supine, prone, or recumbent positions, patient trolley operators should transport the patient trolley to a location that is as close as possible to the surface of the target modality. Additional adjustments can be made by lifting or raising the elevation of the top surface of the patient trolley and transferring the patient using the patient transfer device by sliding the patient transfer device from the top surface of the patient trolley to the top surface of the target modality. MRI environments in particular present obstacles to the use of a patient trolley and transfer device. Due to the tremendous strength of the magnetic field generated by an MRI machine, ferromagnetic materials can present a hazard in an MRI environment and therefore are carefully monitored and typically limited, complicating the construction of any device for use in and around the MRI machine.

Thus, a need exists for improved patient trolleys that not only provide safe transport of patients, but also facilitate easier patient transfer to target modalities within an MRI environment. These and other needs are addressed by the patient trolley and associated systems and methods of the present invention.

SUMMARY OF THE INVENTION

In one aspect of the present invention, a trolley system configured to transport a patient within an MRI environment comprises a patient support portion configured to support the patient, a base portion configured for movement relative to a floor, at least one actuator coupled to the patient support portion and the base portion, the at least one actuator being configured to move the patient support portion relative to the base portion, including but not limited to, changing the elevation of the patient support portion relative to the base portion, and at least one electric motor coupled to the at least one actuator, said actuator causing motion in at least one degree of freedom selected from, but not limited to, a rotary stage, a linear stage, a telescoping stage, a pneumatic stage, a hydraulic stage, a scissor lift, etc. The at least one electric motor may be mounted such that the elevation of the at least one electric motor is fixed relative to the base portion. Furthermore, when the trolley system is positioned adjacent an MRI apparatus within the MRI environment, the magnetic field of the MRI does not interfere with the operation of the at least one electric motor. The trolley may also comprise a plurality of actuators and electric motors.

In another aspect of the present invention, a trolley system configured to transport a patient within an MRI environment comprises a patient support portion configured to support the patient, a base portion configured for movement relative to a floor, and an electric blower coupled to the base portion and fixed to prevent movement of the blower relative to the trolley system, the blower being configured to deliver air to a feature, such as a feature located on the patient transfer device, a feature located on the trolley, an accessory feature, or a feature located on the target modality. When the trolley system is positioned adjacent an MRI apparatus within the MRI environment, the magnetic field of the MRI does not interfere with the operation of the blower.

The trolley system may further comprise a base portion, at least one actuator coupled to the patient support portion and the base portion, and at least one electric motor coupled to the actuator. The at least one actuator may have at least one telescoping stage and be configured to move the patient support portion relative to the base portion and change the elevation of the patient support portion relative to the base portion. The at least one electric motor may be mounted such that the elevation of the at least one electric motor is fixed relative to the base portion, and such that the magnetic field of the MRI does not interfere with operation of the at least one electric motor. The trolley system may also comprise a battery for powering the at least one electric motor and the electric blower. A detachable hose may be used to couple the patient transfer device to the blower.

In yet another aspect of the present invention, a method of delivering a patient to a bore of an MRI device by using a trolley system. The trolley system may include a patient support portion configured to support the patient, a patient transfer device comprising an air bearing on the patient support portion, a base portion configured for movement relative to a floor, an actuator coupled to the patient support portion and the base portion, and one or more electric motors coupled to the actuator, all of the one or more electric motors being mounted such that the elevation of the electric motors is fixed relative to base portion. The method may comprise positioning a trolley system proximate to the bore of the MRI device, such that either end of the trolley system is facing the bore of the MRI device, optionally raising the patient support portion relative to the base portion by actuating the actuator to change the elevation of the patient support portion, providing air to the air bearing, and transferring the patient transfer device from the patient support portion to the target modality, wherein a pull force on the trolley system by a magnetic field of the MRI device is less than or equal to 50 lbs force (and more preferably less than or equal to 25 lbs force) as measured in connection with a nominal 3T MRI device.

In yet another aspect of the present invention, a method of transferring a patient to a target modality within an MRI environment comprises:

positioning a trolley system adjacent the target modality within the MRI environment, the trolley system including a patient support portion configured to support the patient, a patient transfer device comprising an air bearing on the patient support portion, a base portion configured for movement relative to a floor, an actuator coupled to the patient support portion and the base portion, and one or more motors coupled to the actuator, all of the one or more motors being mounted such that the elevation of the motors is fixed relative to base portion, optionally raising the patient support portion relative to the base portion by actuating the actuator to change the elevation of the patient support portion;

providing air to the air bearing; and transferring the patient transfer device from the patient support portion to the target modality, wherein the magnetic field of the MRI does not interfere with the operation of all of the one or more motors during actuation of the actuator.

According to yet another aspect of the present invention, a method of delivering a patient to a bore of an MRI device comprises positioning a trolley system proximate to the bore of the MRI device, such that an end of the trolley system is facing the bore of the MRI device, actuating the electric blower to deliver air to the patient transfer device, thereby supplying air to the patient transfer device to facilitate movement of the patient, and conveying the patient onto a target modality. The trolley system may be MR Compatible with a maximum magnetic attraction force less than or equal to 50 lbs force and include a patient support portion configured to support the patient, a patient transfer device positioned on the patient support portion, a base portion configured for movement relative to a floor, and an electric blower.

In yet another aspect of the present invention, an imaging system is provided comprising an MRI device, a target modality, a trolley system, and a patient transfer device configured for movement relative to a patient support portion of the trolley system.

DETAILED DESCRIPTION OF THE INVENTION

Figure 1:
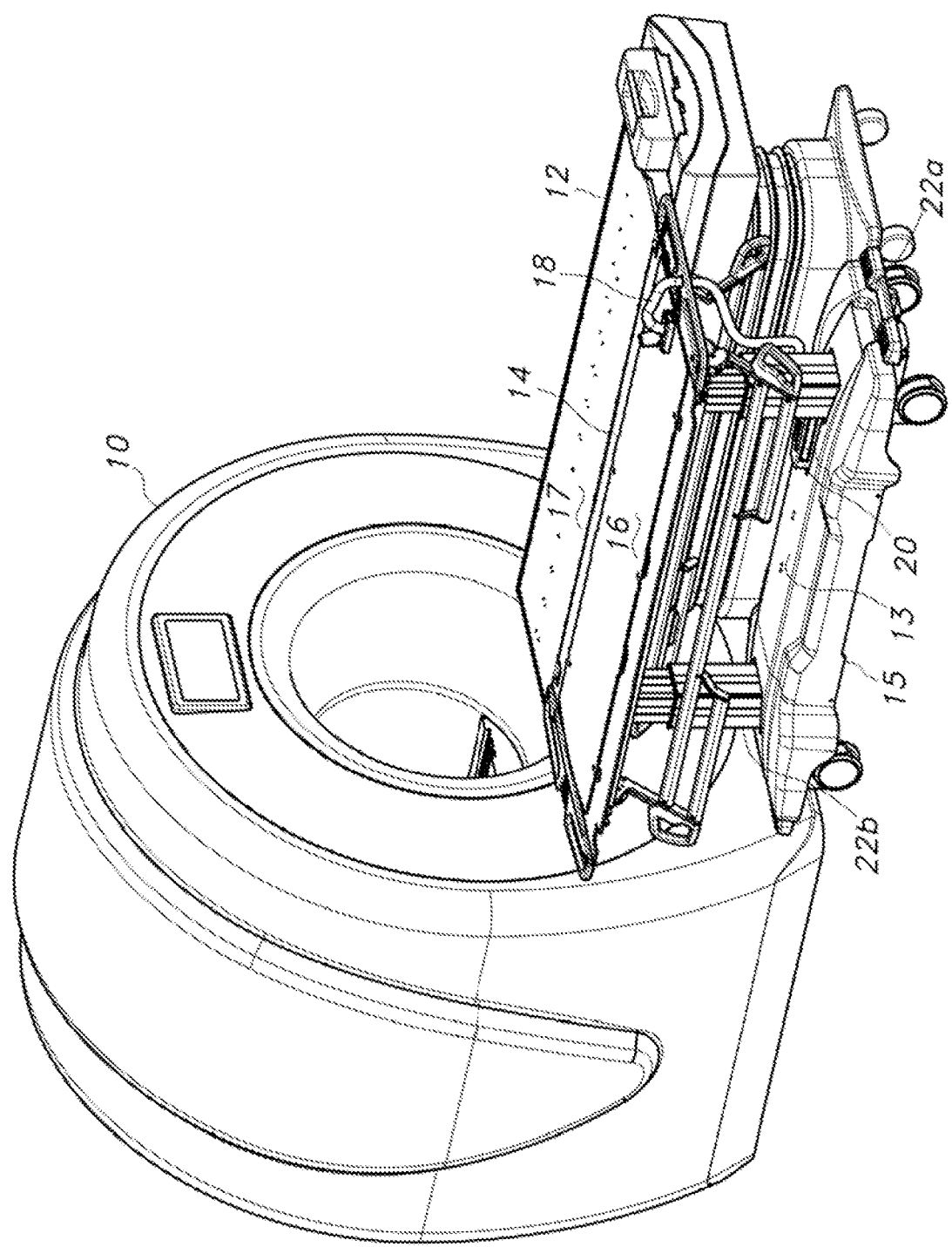
FIG. 1 is a top perspective view of a patient trolley and transfer device according to an embodiment of the present invention next to a target modality in an MRI environment.

The invention is described by reference to exemplary embodiments and variations of those embodiments. Although the invention is illustrated and described herein with reference to specific embodiments, the invention is not intended to be limited to the details shown and described. Rather, various modifications may be made in the details within the scope and range of equivalents of the claims and without departing from the invention.

According to one aspect of this invention, an imaging system is provided comprising an MRI, a target modality, a trolley system, and a patient transfer device configured for movement relative to a patient support portion of the trolley system. The patient transfer device optionally includes an air bearing attached to the underside of the patient transfer device. The imaging system may be combined with a source of low pressure/high volume air coupled to the patient transfer device and configured to deliver air to the air bearing. For example a low pressure/high volume air source may be 0.1 to 5 PSI and 50 to 200 CFM. The air bearing can be of many designs as known to those skilled in the art, including but not limited to, a bladder, a cushion, etc. The trolley system may include at least one actuator, providing at least one degree of motion. The air source provides air flow to the air bearing and facilitates the transfer of the patient from the top surface of the trolley to the patient surface of the target modality.

Also, the trolley system may include an actuator configured to adjust the elevation of a patient support surface relative to a base portion. An actuator may include a lift, a linear stage, a rotary stage, a scissoring mechanism, or any mechanism capable of changing the relative position between two components. The actuator includes, or is coupled to, a motor. When actuated, the motor raises or lowers the elevation of the patient support surface.

Motors for the trolley actuator and blowers used for the operation of the trolley and patient transfer devices may be made of ferromagnetic materials and/or include electrically powered components. The magnetic field can disrupt the operation of the motors, and the ferromagnetic materials can be attracted to the magnetic field of the MRI, thus threatening the safe operation of the trolley and transfer devices. This invention mitigates this risk through placement of the motor and other components to ensure their proper functioning and to reduce magnetic attraction in the MRI environment. As a result, the systems according to the embodiments described herein may be compatible with the MRI environment. As used herein throughout the specification and the claims, the term "MR Compatible" refers to the magnetic attraction force of the trolley system and the operability of one or more electric motors of the trolley system as determined by the MR Compatibility Test Procedure described in the Examples section below.

Regarding the magnetic attraction force of the trolley system, it has been surprisingly discovered that a multi-functional trolley system can be provided according to aspects of this invention while still having a magnetic attraction force that renders the trolley system suitable for use in an MRI environment such as an MRI room. According to embodiments of the invention, the maximum magnetic attraction force is less than or equal to 50 lbs force, and more preferably less than or equal to 25 lbs force, as determined by the MR Compatibility Test Procedure described in the Examples section below.

Regarding the operability of one or more electric motors of the trolley system, it has been surprisingly discovered that a trolley system having one or more electric motors can be provided according to aspects of this invention while still remaining operable in an MRI environment such as an MRI room. According to embodiments of the invention, operability of one or more electric motors of the trolley system is maintained, as determined by the MR Compatibility Test Procedure described in the Examples section below.

Previously, portable blowers have been provided with long hoses for the patient transfer device, so that the blower motor can remain outside of the MRI environment (in practice, outside the MRI room) while the patient is transferred to avoid an unsafe situation. However, it is preferred to avoid the need for such a blower arrangement with long hoses and electrical cords.

By affixing the blower to the trolley according to aspects of this invention, the location and orientation of the blower relative to the MRI machine is controlled such that its function is not impeded. In addition, it has been discovered that the trolley, which is composed primarily of non-ferromagnetic materials, is of sufficient mass that provides an anchoring function for the blower and other features containing ferromagnetic components. This prevents the blower from being dangerously pulled toward and into the MRI machine. Providing a battery power source eliminates the need for electrical cords thereby enabling the unit to be self-contained. Tripping hazards and MRI interference from the electrical cord can also be avoided.

Additionally, it is desirable to optionally use a vacuum pump motor in an MRI environment. Such vacuum pump motors are useful for, among other things, forming vacuum cushions for use during MR imaging. According to aspects of this invention, one or more vacuum pump motors is mounted to the trolley system.

Referring to the Figures, the present invention provides a trolley system 14 configured to transport a patient within an MRI environment such as an MRI room, the trolley system 14 comprises a patient support portion configured to support the patient, stowable side rails 21 on either side of the patient support portion, a base portion 15 configured for horizontal movement relative to a floor, at least one lift or pillar 22a, 22b coupled to the patient support portion and the base portion 15, the at least one lift or pillar 22a, 22b being configured to move the patient support portion relative to the base portion 15 and to change the elevation of the patient support portion relative to the base portion 15, and at least one motor 24a, 24b coupled to the at least one lift 22a, 22b. The at least one motor 24a, 24b is mounted such that the elevation of the at least one motor 24a, 24b is fixed, or limited, relative to the base portion 15, and the trolley system 14 is positionable adjacent an MRI apparatus 10 within the MRI environment and the magnetic field of the MRI 10 does not interfere with the operation of the at least one lift 22a, 22b, or at least one blower 19. Alternatively, the motor of the at least one lift 22a, 22b may be mounted to the lower portion of the lift in such a way that the displacement of the motor with respect to the base portion is limited or prevented, such that the motor remains within a weaker portion of the magnetic field.

In another embodiment of the present invention, a trolley system 14 configured to transport a patient within an MRI environment comprises a patient support portion configured to support the patient, a patient transfer device 16 configured for movement relative to the patient support portion, the patient transfer device 16 providing an air bearing, and a blower 19 coupled to the patient transfer device 16 and fixed to prevent movement of the blower 19 relative to the trolley system 14, the blower 19 being configured to deliver air to at least one feature of the trolley system 14 (such as the air bearing). The feature may be selected from the group consisting of a patient transfer device or other accessory features, such as a patient bed, a wound care bed, a bed that provides alternating pressures, a surface designed for therapeutic applications, a surface designed for patient comfort, a skin protection surface, an air powered device, and a compression surface. The feature may also include other accessories known to one skilled in the art. The trolley system 14 is positionably adjacent an MRI apparatus 10 within the MRI environment and the magnetic field of the MRI 10 does not interfere with the operation of the blower 19.

Referring to each of the figures more specifically, wherein like reference numerals used in the figures denote like parts throughout the various figures, a patient trolley 14 according to an embodiment the present invention is illustrated in FIG. 1 within an MRI environment. The patient trolley 14 is adjacent to an MRI table 12 and is located near the bore of an MRI machine 10. The patient trolley 14 includes a patient transfer device 16 to facilitate transfer from the top of the patient trolley 14 to the patient support surface 17 of the MRI table 12. The base portion 15 of the patient trolley 14 includes a connecting hub 20 to provide a connection via a hose 18 to the patient transfer device 16. The connecting hub 20 also provides a portal facilitating connections between the system electronics and the top of the patient trolley 14.

Transfer of a patient from the patient trolley 14 to the MRI table 12 is facilitated by delivering air to an air bearing (not shown) on the underside of the patient transfer device 16 by using the blower 19. This air bearing reduces the friction between the patient transfer device and the surface along which it travels.

Figure 2:
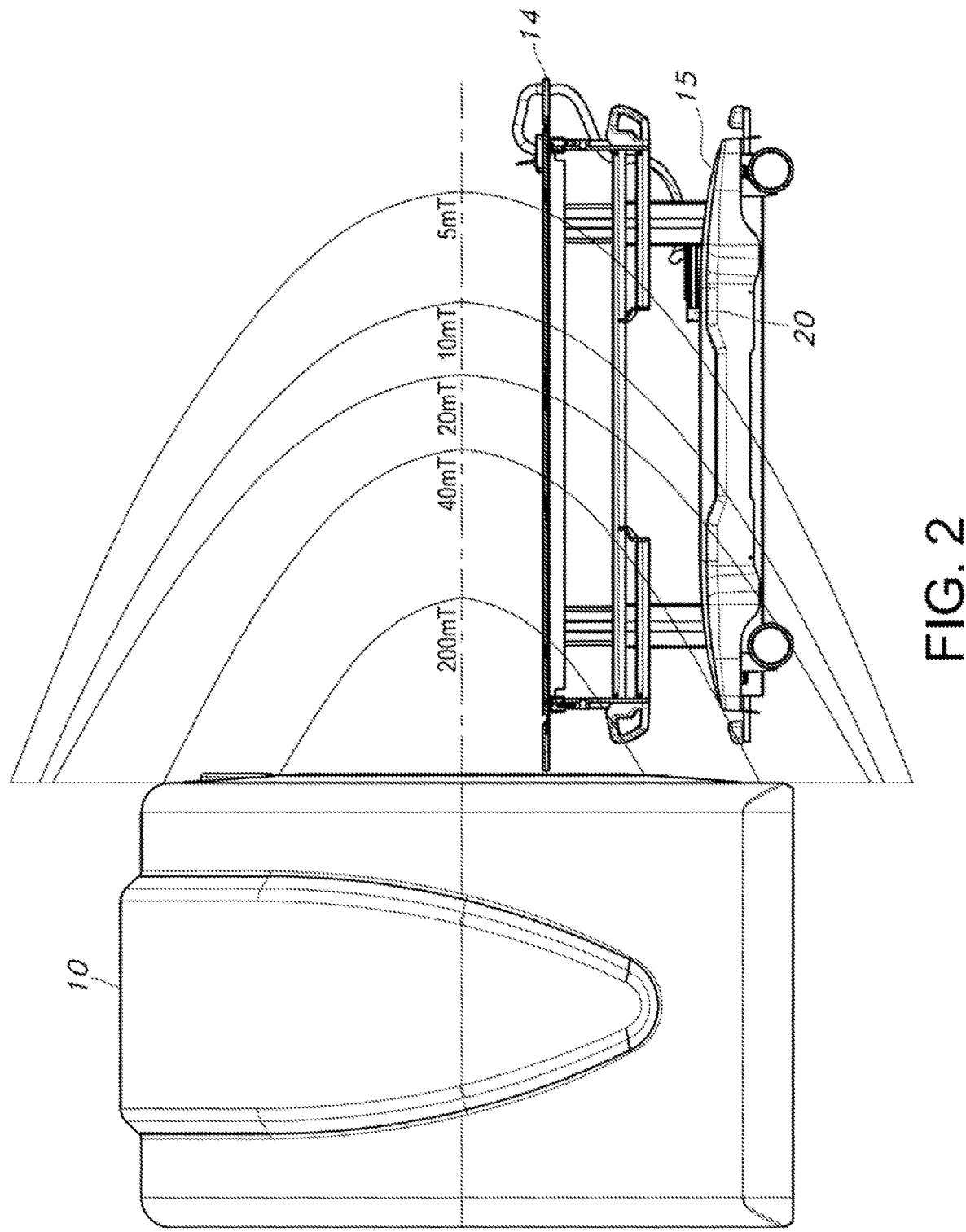
FIG. 2 is a side view of the patient trolley and transfer device of FIG. 1 within a magnetic field of an MRI machine.

The magnetic field strength of most commercial MRI machines used for diagnostic imaging for humans is within the range of 0.35 to 3 Tesla. However, this rating only describes the maximum strength of the magnetic field within the bore of the MRI machine. As illustrated in the schematic illustration of FIG. 2, the magnetic field strength of the MRI machine 10 decreases with distance. The force exerted on any ferromagnetic components is related to the field strength where the components are located. Because portions of the patient trolley will be close to the bore of the MRI machine when the patient trolley is in position to transfer the patient, it is preferred that non-ferromagnetic materials are used to manufacture the patient trolley, particularly the top and leading portions of the patient trolley, which will be in close proximity to the MRI machine.

Due to physical property requirements or cost demands, it may be impractical to include components made solely from non-ferromagnetic materials. In order to further minimize the potential effects of the magnetic field from the MRI machine on the patient trolley, the components, specifically the components having moving parts, are configured, such that the components remain fixed or at least are positioned near the base of the patient trolley. Assuming that the MRI machine has the magnetic field profile of a typical 3T machine (such as the magnetic field profile illustrated in FIG. 2), the base portion 15 of the patient trolley 14 will be exposed to magnetic field strengths generally no greater than 200 mT due to the location of the base portion 15 relative to the MRI machine 10.

Figure 3:
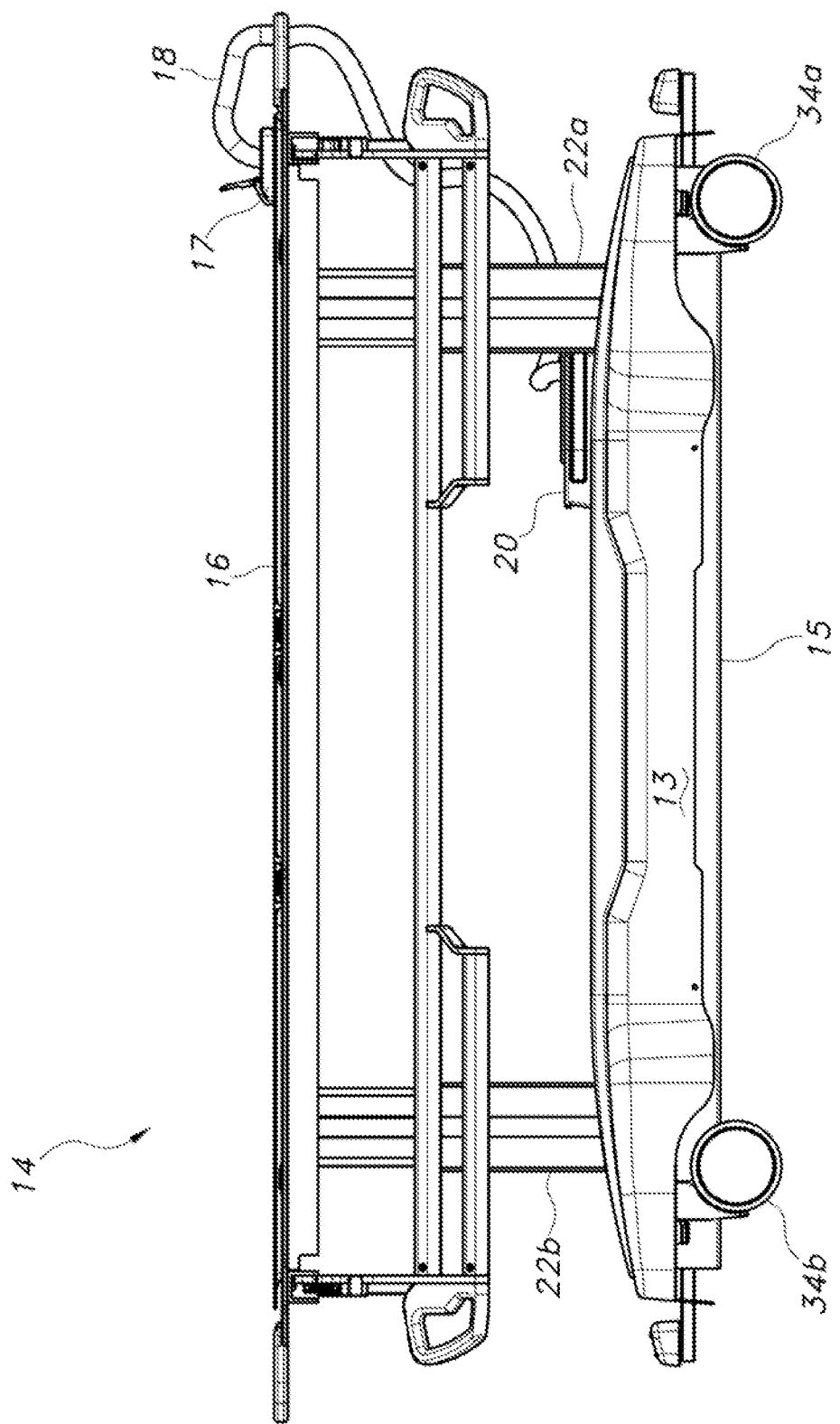
FIG. 3 is a side view of the patient trolley and transfer device of FIG. 1.
Figure 4:
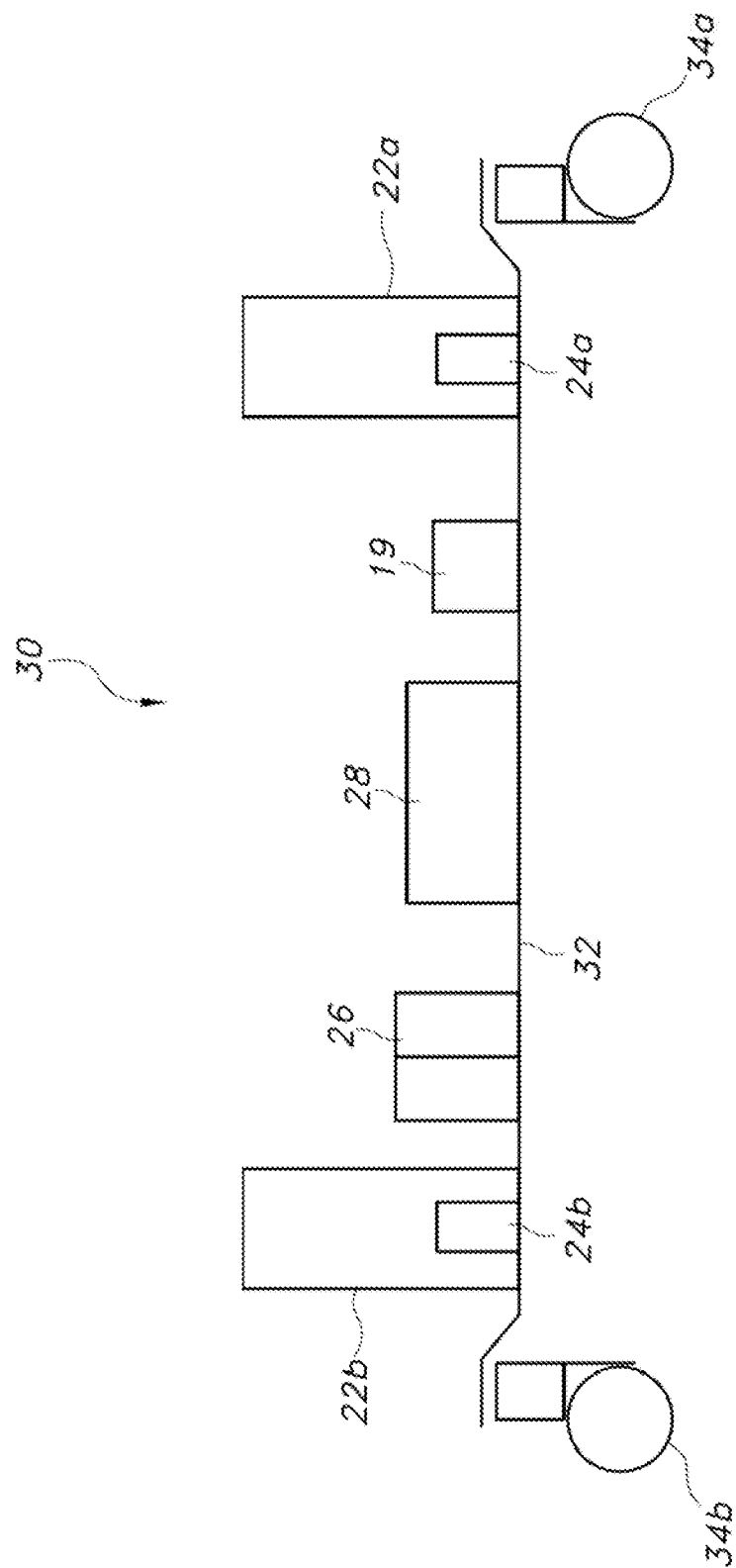
FIG. 4 is a schematic side view of the chassis of a patient trolley according to another embodiment of the present invention.
Figure 5:
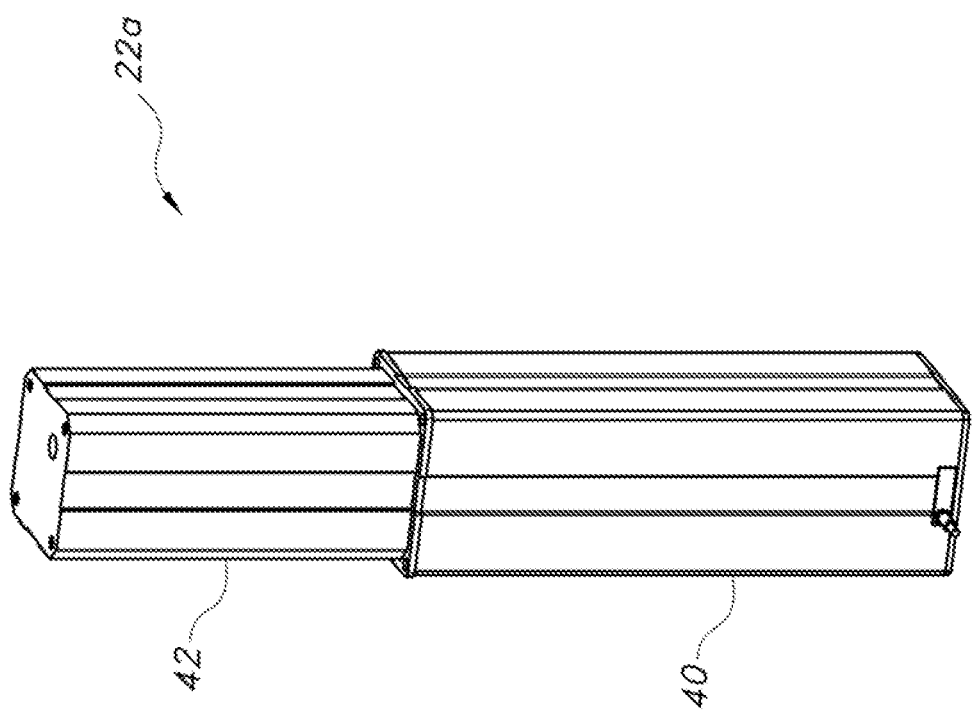
FIG. 5 is a top perspective view of an embodiment of a lift or actuator for a patient trolley according to another embodiment of the present invention.

Referring now to the embodiment illustrated in FIGS. 3 to 5, the patient trolley 14 includes a top portion having a top surface on which a patient transfer device 16 is located. Stowable side rails 21 are also located along the sides of the top portion. The patient transfer device 16 includes a hose connector 17 to receive one end of a hose 18. The hose 18 preferably has two sections. The top section has two opposing ends in which one end is connected to the hose connecter 17 of the patient transfer device 16 and the opposite end is connected to a top portion of the trolley 14. The bottom section of the hose 18 also has two opposing ends with one end being connected to the top portion of the trolley 14 and the opposite end connected to a blower 19 located in the base portion 15 of the patient trolley 14, and should be of sufficient length to provide enough slack to accommodate the full height range of the trolley top 14. While various blowers can be utilized, one exemplary blower is available from AMETEK Corp. (e.g., AMETEK Lamb Electric 116157-00). The top section of the hose 18 should be of sufficient length to provide enough slack such that the hose 18 remains attached to the patient transfer device 16 when the patient transfer device 16 is transferred from the top surface of the patient trolley 14 to the patient surface of the target modality (e.g., an MRI table). The top section of the hose 18 may also be disconnected when not in use.

Two telescoping pillars 22a, 22b are connected to the underside of the top portion and the base portion 15 of the patient trolley 14. The pillars 22a, 22b are telescoping, so that the elevation of the top surface, and consequently the patient transfer device 16, may be adjusted relative to the base portion 15. For example, according to one exemplary embodiment of the invention, pillars 22a, 22b may include a telescopic pillar such as the TELEMAG TLG system of SKF Group (e.g., model no. TLG 10/11-A, TLG 10/11-B, and TLG 10/11-C or other similar models such as SKF TLG10-CA34F-000). As understood by those of skill in the art, the patient trolleys according various embodiments of the invention may include only one pillar or, alternatively, two or more pillars.

To ensure safe transfer of a patient from the patient trolley to the target modality, the elevation of the top surface of the patient trolley should be about equal to the elevation of the patient surface of the target modality. The base portion 15 may include a plurality of castors or wheels 34a, 34b, so that the trolley system is positionable adjacent the MRI apparatus within the MRI environment. The wheels 34a, 34b are preferably in the form of casters for optimal maneuverability. For example, the wheels 34a, 34b according to one exemplary embodiment include castors provided by Darcor Limited of Toronto, Canada (e.g., model no. T-CLM6-PD). The base portion 15 may include an optional cover 13 that acts as a housing within which various components of the patient trolley 14 are mounted.

Referring to FIG. 4, a schematic representation of the base portion 15 of another embodiment of the present invention is provided. In the embodiment of FIG. 4, the cover 13 has been excluded from the base portion 15 revealing the components within the uncovered base portion 30. Mounted to the base 32 of the uncovered base portion 30 are two actuators 22a, 22b, actuator motors 24a, 24b, blower 19 (and/or vacuum pump), battery pack 26, and control unit 28. The plurality of wheels 34a, 34b may also be attached to the underside of the base portion 15. The battery pack 26 is connected to the actuator motors 24a, 24b, blower 19, and control unit 28, thereby providing sufficient power to operate the system. Types of batteries include, but are not limited to, lithium ion, lead acid, and nickel cadmium, the preferred embodiment being lithium ion.

As explained above, it is preferred that the motors, blower, control unit, and/or battery pack are mounted to the base portion to minimize the effect of the magnetic field of the MRI on the operation of the motors during use of the actuator or the blower during a patient transfer. In one embodiment, the blower may be mounted on the underside of the trolley top as the blower is normally not required to operate while the actuators are moving, which would cause the running motor to be moving through the magnetic field of the MRI, creating additional induced current. The blower can optionally be positioned in a weaker portion of the magnetic field. For example, mounting the blower closer to the distal end of the patient trolley relative to the MRI machine minimizes the potential for interference by the magnetic forces on the blower. More preferably, the components in the base of the patient trolley are mounted, such that the elevation of one or more of these components is fixed relative to the floor upon which the patient trolley travels. Alternatively, the elevational travel of the components can be permitted and limited. For systems in which it is desirable to have the trolley configuration be symmetric from one operator end to the other, it is possible to mount the electronic components near the centerline of the trolley between each end. This minimizes the strength of the magnetic field to which the electronics are subjected when moved into the MRI machine in either orientation.

According to various embodiments of the present invention, it is preferred to include a blower that is firmly attached to the trolley, i.e. not separately portable. A separately portable blower is likely to contain ferromagnetic material and when not firmly attached to the trolley can pose a severe risk of becoming a projectile in an MRI environment.

It is possible for the magnetic forces generated by the MRI machine to overcome the force of gravity or the force holding such a blower in position because the mass of the blower is not sufficient to resist the attraction force generated by the MRI machine. If the blower is not maintained at a safe distance from the MRI machine, the blower may be attracted by and pulled into the bore of the MRI machine. This is a potentially dangerous occurrence because the blower may strike and injure an operator or patient that is also in the vicinity of the MRI machine. It may also damage the MRI machine or the blower itself. Previously, blowers have been placed outside the room in which the MRI is located to mitigate this risk.

Therefore, it is preferable that various embodiments of the patient trolley according to the present invention include a blower that is fixed on the patient trolley, preferably at a position that will remain at a distance from the MRI machine at which the MRI will not interfere with the functioning of the blower motor. Furthermore, it has been discovered that the configuration of the blower's location on the patient trolley according to the various embodiments of the present invention reduces the magnetic attraction force created by the ferromagnetic components of the blower.

Similarly, if the blower for the patient transfer device and the motor or motors used to operate the actuator of the patient trolley include electric motors, the strength of the MRI machine also has the potential to disrupt the operation of the motors. As understood by those of skill in the art, electric motors typically utilize magnetic fields to produce mechanical motion, providing a driving mechanism. These motors can contain both electromagnets and fixed magnets. These electric motors may be disrupted by an external magnetic field. Therefore, the configuration of the motor and blower in the base of the patient trolleys according to various embodiments of the present invention are necessary to ensure proper functioning of the lifting mechanism and delivering air to the patient transfer device.

As explained above, the blower is preferably mounted in the base of the patient trolley sufficiently far away from the bore of the MRI machine, such that the magnetic field of the MRI does not interfere with the operation of the blower. With respect to the pillar motors, some lifting mechanisms include multiple stages with a motor incorporated in each elevating lift of the stage. In such a configuration, the operation of the electric motor may be disrupted by the magnetic field of the MRI machine, if the motor is elevated to a position within a strong field or, forced to operate while moving through a strong magnetic field. For various embodiments of the present invention, it is preferred to use an actuator that is configured, such that the motor remains at or within the base portion of the patient trolley. This may be achieved by using an embodiment of the pillars as illustrated in FIG. 5.

In FIG. 5, pillar 22a is illustrated in an extended position. The pillar 22a is preferably limited to two sections, a bottom section 40 that is mounted to the base of the patient trolley, and a top section 42, which is telescoping and moves relative to the bottom section 40. The motor for the pillar 22a may be mounted within the bottom section 40 of the pillar 22a, such that the elevation of the motor does not change as the top section 42 is raised. As understood by one of skill in the art, the materials used to fabricate the pillar should be selected to accommodate the weight of the top portion of the patient trolley in addition to the weight of a patient transfer device and a patient. The pillar motors should also be selected, such that the motors are able to generate sufficient power to safely raise and lower the patient. If a pillar containing more than two sections is used, it is preferable to employ a mechanism that allows the motor or motors to remain stationary while driving the moving sections.

According to another embodiment of the present invention, a method of transferring a patient to a target modality within an MRI environment is provided. The method comprises first positioning a trolley system adjacent the target modality within the MRI environment. The trolley system comprises a patient trolley having a patient support surface and a base portion. Positioning includes ensuring that the patient support surface is about parallel and adjacent to the patient support surface of the target modality. Next, a user may optionally raise the patient support portion relative to the base portion by actuating a lift to change the elevation of the patient support portion relative to the base portion. This may be optional because in certain circumstances the height of the patient support portion may be approximately equal to the height of the target modality, therefore adjustment is not necessary in such circumstances. In fact, a fixed height trolley (without motor and actuator) may be provided according to aspects of this invention. Alternatively, the height of the target modality may be adjusted to be approximately equal to the height of the patient support portion. If the trolley system also includes a patient transfer device on the patient support surface, the method further comprises providing air to the air bearing of the patient transfer device and transferring the patient transfer device from the patient support portion to the target modality.

EXAMPLES

Advantageous properties of aspects of this invention can be observed by reference to the following examples, which illustrate but do not limit the invention.

MR Compatibility Test Procedure

Figure 6:
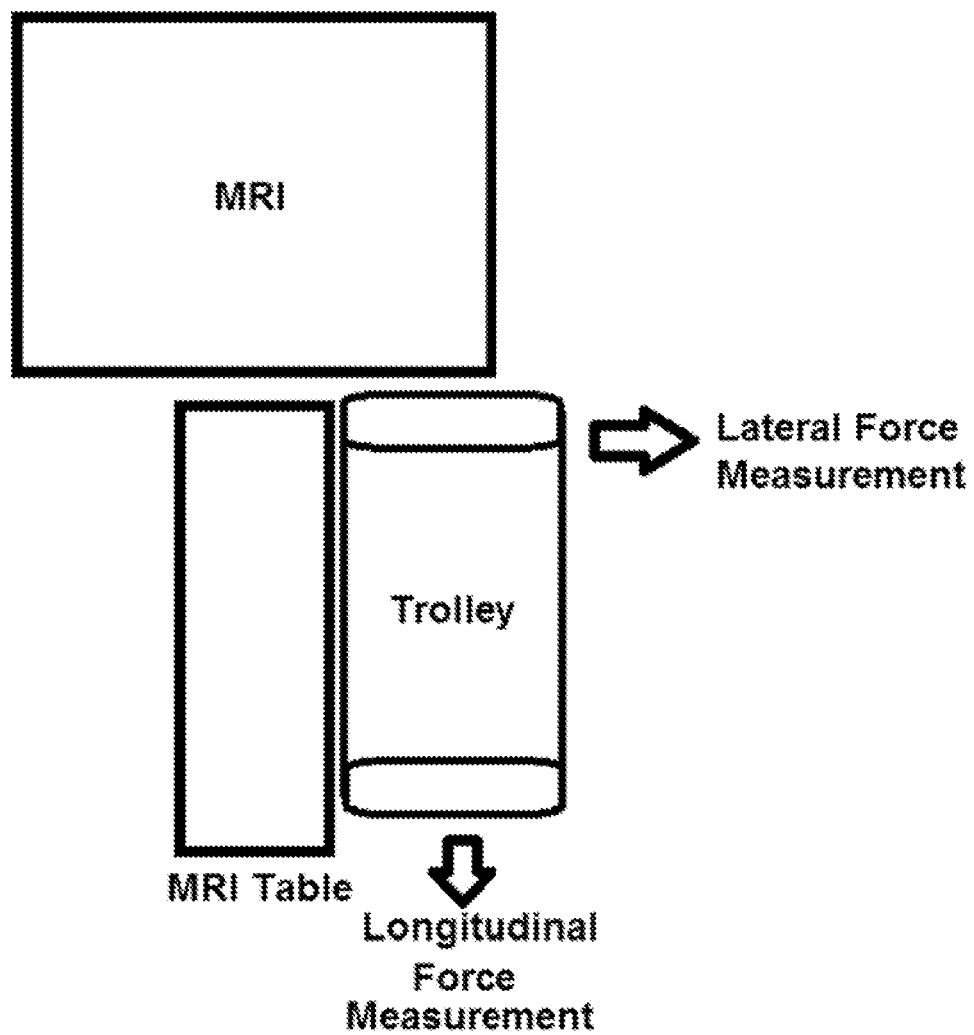
FIG. 6 is a schematic top plan view of the relative position of a trolley and an MRI device when determining the pull force on the trolley system.

The following MR Compatibility Test Procedure is used to determine MR Compatibility according to aspects of this invention. It is used to determine the magnetic attraction force of a trolley system as well as the operability of one or more electric motors included in the trolley system. Reference is made to FIG. 6, which illustrates schematically the relative position of a trolley system and an MRI device.

I. Test Setup

Place the trolley system on a hard flat surface (such as a linoleum floor), ensuring that brakes of the trolley system are in their unlocked position.

II. Procedure

A. Testing Equipment

The MRI device used is a Siemens MAGNETOM Verio 3T MRI scanner device or equivalent nominal 3T MRI scanner with a horizontal $B_0$ orientation. Other equivalent nominal 3T MR scanners are available from Siemens, GE, Philips, Toshiba and others.

B. Trolley Orientation—Gantry End against Bore

Lower the trolley system to its lowest position. Orient the trolley such that the gantry end is facing the bore of the magnet and the trolley is parallel to the MRI table. Slowly introduce the trolley into the magnetic field until the gantry end is against the face of the bore, or the gantry end is as close as possible to the magnet.

C. Force Measurement

Using a force gauge, ensure there is no load on the gauge and verify the dial is zeroed. To zero the gauge, rotate the dial face so that the gauge needle rests above the zero mark.

At the locations described in FIG. 6, use the force gauge to pull the trolley horizontally away from the bore of the magnet until the trolley begins to move and record the Lateral Force Measurement and the Longitudinal Force Measurement.

Repeat these measurements with the trolley in its highest pillar position.

D. Electronic Functionality Test

While the trolley is against the face of the bore in the position shown in FIG. 6, verify that each of the following electronic systems function, if present in the tested trolley.

1. Pillar Travel

For a trolley system having height adjustment with one or more electric motors, test the operation of those motors. For example, using 'up' and 'down' arrows on a control panel of one embodiment of the trolley system, move the pillars from their lowest position to their highest position. For embodiments with plural pillars, the pillars should reach their full extent of travel synchronized with each other.

2. Blower Activation

For a trolley system having one or more blowers with electric motors, test the operation of those motors. Put the brakes in their locked position. Actuate the blower(s). Actuating any of the blowers should cause the blower to turn on and air to travel down the hose.

3. Vacuum Activation

For a trolley system having one or more vacuum pumps with electric motors, test the operation of those motors. Put the brakes in their locked position.

Actuate the vacuum pump(s). Actuating any of the vacuum pumps should cause the actuated vacuum pump to turn on and produce vacuum.

E. Trolley Orientation—Operator End against Bore

Lower the trolley to its lowest position. Orient the trolley such that the operator end is facing the bore of the magnet and the trolley is parallel to the MRI table. Slowly introduce the trolley into the magnetic field until the operator end is against the face of the bore, or the operator end is a close as possible to the magnet.

Repeat the Force Measurement and Electronic Functionality Test above.

Example 1

In order to determine the magnetic attraction force of a trolley system made according to an embodiment of the present invention, a trolley similar to the embodiment illustrated in FIG. 3 was tested proximate to a Siemens MAGNETOM Verio 3T MRI device. A Siemens MAGNETOM Espree 1.5T MRI device was also used for comparison purposes. The trolley included stowable rails 21, lifts 22a, 22b, as well as a memory system in order to store multiple pre-selected positions for the lifts 22a, 22b. The operator end of the trolley is the right-side end of the trolley in the view provided in FIG. 3, where the hose 18 is located, and the gantry end is the left-side end. The trolley 14 was introduced into the magnetic field until the gantry end was against the face of the bore. At the locations illustrated in FIG. 6, the brakes on the trolley were disengaged and a force gauge was used to pull the trolley 14 away from the bore of the magnet until the trolley 14 began to move and the maximum force was recorded. This procedure was repeated after extending the lifts 22a, 22b to raise the trolley 14 to its highest elevation and deploying the side rails 21 to the raised position. The procedure was repeated again with the trolley 14 in the raised and lowered positions after turning the trolley 14 180 degrees, such that the operator end of the trolley 14 was against the bore of the MRI.

The results of the force measurement testing are provided in the following table:

|  | MRI (T) | Trolley Configuration | Pull Direction | Force Measurement (lbs force) |
|---|---|---|---|---|
| Gantry End Against Bore | 1.5 | Lowered | Lateral | 7 |
|  | 1.5 | Lowered | Longitudinal | 6 |
|  | 1.5 | Raised | Lateral | 5 |
|  | 1.5 | Raised | Longitudinal | 10 |
|  | 3 | Lowered | Lateral | 10 |
|  | 3 | Lowered | Longitudinal | 10 |
|  | 3 | Raised | Lateral | 9.5 |
|  | 3 | Raised | Longitudinal | 12 |
| Operator End Against Bore | 1.5 | Lowered | Lateral | 5.5 |
|  | 1.5 | Lowered | Longitudinal | 5 |
|  | 1.5 | Raised | Lateral | 7 |
|  | 1.5 | Raised | Longitudinal | 7 |
|  | 3 | Lowered | Lateral | 8 |
|  | 3 | Lowered | Longitudinal | 11 |
|  | 3 | Raised | Lateral | 10 |
|  | 3 | Raised | Longitudinal | 11 |

In each of the four orientations described above, the function of the electronic systems was tested in proximity of the 1.5T and 3T MRI. The electromechanical functions of the following user-interfacing components were tested: the blower, the vertical operation of the pillar, the memory control of the pillar height, a pillar calibration module, the control panel, an alarm, a main power switch, and a safety interlock. In a first test, the pillars 22a, 22b were lowered and raised from their lowest to highest positions. In a second test, four separate memory positions for the pillars 22a, 22b were selected to determine if the trolley was able to correctly alternate between the various height settings. In a third test, an automatic calibration mode of the pillars 22a, 22b was performed. In a fourth test, the blower was operated while the brakes on the trolley wheels were engaged to test the functioning of a safety interlock. In a fifth test, the blower was operated while the brakes were disengaged to test the functioning of an alarm. In a sixth test, a control panel stop function was tested to determine whether the control panel and blower buttons would remain unresponsive. In a seventh test, the main power switch was toggled to determine whether the electronic system was able to start up normally. All of the electronic functions of the trolley 14 operated correctly and exhibited no interference while in proximity of either MRI magnet.

According to one aspect of the invention, a trolley system is configured to transport a patient within an MRI room, the trolley system comprising: a patient support portion configured to support the patient; a base portion configured for movement relative to a floor; at least one actuator coupled to the patient support portion and the base portion, the at least one actuator being configured to move the patient support portion relative to the base portion and to change the elevation of the patient support portion relative to the base portion; and at least one electric motor coupled to the at least one actuator, wherein the at least one electric motor is mounted such that the elevation of the at least one electric motor is fixed relative to the base portion; wherein the trolley system is MR Compatible with a maximum magnetic attraction force less than or equal to 50 lbs force.

According to another aspect of the invention, a trolley system is configured to transport a patient within an MRI room, the trolley system comprising: a patient support portion configured to support the patient; a base portion configured for movement relative to a floor; and an electric blower coupled to the base portion of the trolley system and fixed to prevent movement of the electric blower relative to the trolley system, the electric blower being configured to deliver air to a feature of the trolley system; wherein the trolley system is MR Compatible with a maximum magnetic attraction force less than or equal to 50 lbs force.

According to another aspect of the invention, a method of delivering a patient to a bore of an MRI device is provided, the method comprising: positioning a trolley system proximate to the bore of the MRI device, such that an end of the trolley system is facing the bore of the MRI device, the trolley system being MR Compatible with a maximum magnetic attraction force less than or equal to 50 lbs force and including a patient support portion configured to support the patient, a base portion configured for movement relative to a floor, an actuator coupled to the patient support portion and the base portion, and one or more electric motors coupled to the actuator; optionally raising the patient support portion relative to the base portion by actuating the actuator to change the elevation of the patient support portion relative to the base portion; and conveying the patient onto a target modality.

According to another aspect of the invention, an imaging system is provided comprising: an MRI device; and a trolley system according to aspects of this invention.

According to another aspect of the invention, a trolley system is configured to transport a patient within an MRI environment, the trolley system comprising: a patient support portion configured to support the patient; a base portion configured for movement relative to a floor; at least one actuator coupled to the patient support portion and the base portion, the at least one actuator being configured to move the patient support portion relative to the base portion and to change the elevation of the patient support portion relative to the base portion; and at least one electric motor coupled to the at least one actuator; wherein the at least one electric motor is mounted such that the elevation of the at least one electric motor is fixed relative to the base portion; and wherein the trolley system is positionable adjacent an MRI apparatus within the MRI environment and the magnetic field of the MRI does not interfere with the operation of the at least one electric motor.

According to another aspect of the invention, a trolley system is configured to transport a patient within an MRI environment, the trolley comprising: a patient support portion configured to support the patient; an electric blower coupled to a feature of the trolley system and fixed to prevent movement of the electric blower relative to the trolley system, the electric blower being configured to deliver air to the patient transfer device; wherein the trolley system is positionable adjacent an MRI apparatus within the MRI environment and the magnetic field of the MRI does not interfere with the operation of the electric blower.

According to another aspect of the invention, a method of transferring a patient to a target modality within an MRI environment is provided, the method comprising: positioning a trolley system adjacent the target modality within the MRI environment, the trolley system including a patient support portion configured to support the patient, a patient transfer device comprising an air bearing on the patient support portion, a base portion configured for movement relative to a floor, an actuator coupled to the patient support portion and the base portion, and one or more electric motors coupled to the actuator, all of the one or more electric motors being mounted such that the elevation of the electric motors is fixed relative to base portion; optionally raising the patient support portion relative to the base portion by actuating the actuator to change the elevation of the patient support portion relative to the base portion; delivering air to the air bearing; and transferring the patient transfer device from the patient support portion of the trolley to the target modality; wherein the magnetic field of the MRI does not interfere with the operation of all of the one or more electric motors during actuation of the actuator.

According to another aspect of the invention, a method of delivering a patient to a bore of an MRI device is provided, the method comprising positioning a trolley system proximate to the bore of the MRI device, such that an end of the trolley system is facing the bore of the MRI device, the trolley system being MR Compatible with a maximum magnetic attraction force less than or equal to 50 lbs force and including a patient support portion configured to support the patient, a patient transfer device positioned on the patient support portion, a base portion configured for movement relative to a floor, and an electric blower, actuating the electric blower to deliver air to the patient transfer device, thereby supplying air to the patient transfer device to facilitate movement of the patient; and conveying the patient onto a target modality.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A trolley system configured to deliver air within an MRI room, the trolley system comprising:
    a base portion configured for movement relative to a floor; and
    an electric blower coupled to the base portion of the trolley system and fixed to prevent movement of the electric blower relative to the trolley system, the electric blower being configured to deliver air, and an elevation of the electric blower does not change when the blower delivers air, the electric blower being mounted such that the electric blower remains within a weaker portion of a magnetic field generated by an MRI apparatus in the MRI room, thereby reducing the effect of the magnetic field on the operation of the electric blower during use of the electric blower; and
    a battery for powering the electric blower;
    wherein the electric blower is configured to deliver air to a patient transfer device to facilitate movement of the patient transfer device relative to a patient support;
    wherein the trolley system is MR Compatible with a maximum magnetic attraction force less than or equal to 50 lbs force; and
    wherein the trolley system is positionable adjacent the MRI apparatus within the MRI environment and the magnetic field of the MRI apparatus does not interfere with the operation of the electric blower when the trolley system is positioned adjacent the MRI apparatus, such that the electric blower operates while adjacent the MRI apparatus and while the magnetic field is generated by the MRI apparatus.

2. A method of moving a patient relative to a bore of an MRI device using a patient transfer device, the method comprising:
    positioning a trolley system proximate to the bore of the MRI device, the trolley system being MR Compatible with a maximum magnetic attraction force less than or equal to 50 lbs force and including
        a base portion configured for movement relative to a floor, and
        an electric blower,
    actuating the electric blower to deliver air to the patient transfer device, thereby supplying air to the patient transfer device to facilitate movement of the patient; and moving the patient and the patient transfer device relative to the bore of the MRI device.

3. The trolley system of claim 1, the electric blower being configured to deliver air to an air bearing of the patient transfer device.

4. The trolley system of claim 1, further comprising plural wheels positioned for movement of the trolley system relative to the floor.

5. The trolley system of claim 1, wherein the trolley system is MR Compatible with a maximum magnetic attraction force less than or equal to 25 lbs force.

6. The trolley system of claim 1, the electric blower being mounted to a lower portion of the trolley system.

7. The trolley system of claim 6, wherein at least one of the battery and the electric blower is located within a central region of the base portion.

8. The trolley system of claim 1, the trolley system being configured to transport a patient, the trolley system further comprising a patient support portion configured to support the patient.

9. The trolley system of claim 1, wherein air is delivered from the electric blower to at least one of a patient transfer device, a patient bed, a wound care bed, a bed that provides alternating pressures, a surface designed for therapeutic applications, a surface designed for patient comfort, a skin protection surface, an air powered device, and a compression surface.

10. The trolley system of claim 1, wherein the electric blower of the trolley system is configured to be coupled to a patient transfer device for providing air to an air bearing.

11. The trolley system of claim 10, wherein the electric blower is couplable to the patient transfer device via a hose of the trolley system.

12. The trolley system of claim 11, wherein the hose is detachable from the trolley system.

13. The method of claim 2, the trolley system including a patient support portion configured to support the patient, the method further comprising moving the patient and the patient transfer device relative to the patient support portion.

* * * * *